US00PP13964P29

(12) United States Plant Patent
Utecht

(10) Patent No.: US PP13,964 P2
(45) Date of Patent: Jul. 8, 2003

(54) GERANIUM PLANT NAMED 'FIP 440'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/259,748

(22) Filed: Sep. 30, 2002

(51) Int. Cl.[7] ..... A01H 5/00
(52) U.S. Cl. ..... Plt./327

(58) Field of Search ..... Plt./327

*Primary Examiner*—Kent Bell
(74) *Attorney, Agent, or Firm*—Foley & Lardner

(57) ABSTRACT

A new and distinct cultivar of geranium plant named 'Fip 440' characterized by the combined features of brilliant orange, semi-double flowers, large inflorescences, long, strong peduncles, medium green, distinctly zoned foliage, moderately vigorous growth, round and bushy plant habit, and medium to somewhat late flowering response.

1 Drawing Sheet

Latin name of the genus and species of the plant claimed: *Pelargonium zonale L'Héritier.*
Variety denomination: 'Fip 440'.

BACKGROUND OF THE INVENTION

The present invention comprises a new and distinct cultivar of geranium, botanically known as *Pelargonium zonale*, and hereinafter referred to by the cultivar name 'Fip 440'.

'Fip 440' is a product of a planned breeding program which had the objective of creating new orange semi-double flowers, deep green zoned foliage and vigorous, but well-branched growth habit.

'Fip 440' originated from a hybridization made by the inventor Angelika Utecht in a controlled breeding program in Galdar, Gran Canaria, Spain, in 1996. The female parent was the unpatented hybrid seedling, no. 92-990-1, having orange-red single-type flowers, medium green foliage with relatively strong zonation, and compact to medium plant habit. The male parent of 'Fip 440' was the unpatented hybrid seedling no. 93-686-37, characterized by deep salmon, semi-double flowers, dark green foliage with weak zonation, and medium growth habit.

'Fip 440' was selected as one flowering plant within the progeny of the stated cross by Angelika Utecht in 1997 in a controlled environment in Galdar, Gran Canaria, Spain. The first act of asexual reproduction of 'Fip 440' was accomplished when vegetative cuttings were taken from the initial selection in the fall of 1997 in a controlled environment in Galdar, Gran Canaria, Spain, by, or under the supervision of, Angelika Utecht.

Horticultural examination of plants grown from cuttings of the plant initiated in May 1998 in Hillscheid, Federal Republic of Germany, and continuing thereafter, has demonstrated that the combination of characteristics as herein disclosed for 'Fip 440' are firmly fixed and are retained through successive generations of asexual reproduction.

'Fip 440' has not been observed under all possible environmental conditions. The phenotype may vary significantly with variations in environment such as temperature, light intensity and day length.

The following observations, measurements, and comparisons describe plants grown in Hillscheid, Germany, and in Langley, British Columbia, Canada, under greenhouse conditions which approximate those generally used in commercial practice.

BRIEF SUMMARY OF THE INVENTION

The following traits have been repeatedly observed and are determined to be basic characteristics of 'Fip 440' which, in combination, distinguish this geranium as a new and distinct cultivar:

1. Brilliant orange-red flowers;
2. large inflorescences on strong peduncles high above the foliage;
3. medium-green foliage, large leaves with distinct zonation;
4. moderately vigorous growth, tall and rounded, only moderately wide plant habit; and
5. medium to moderately late spring flowering response.

Of the many commercial cultivars known to the present inventor, the most similar in comparison to 'Fip 440' is the unpatented, related variety 'Fisnida' and 'Fisglo' (U.S. Plant Pat. No. 7,394), and the unpatented commercial variety 'Fisglori'.

In comparison to 'Fisnida', 'Fip 440' has semi-double flowers, while those of 'Fisnida' are single-type and a somewhat deeper red hue. Furthermore, 'Fisnida' grows more vigorously, and inflorescences are borne on even longer peduncles. In comparison to 'Fisglo', 'Fip 440' has similar flowers, but foliage with stronger zonation, and growth is much more vigorous, with the umbels higher above the foliage.

In comparison to 'Fisglori', 'Fip 440' has a somewhat lighter orange hue of flower color but more intense coloring on the lower side of petals, while petal undersides of 'Fisglori' appear almost white. In addition, foliage of 'Fip 440' is more distinctly zoned, and plant habit is taller with the inflorescences higher above the foliage.

BRIEF DESCRIPTION OF THE DRAWING

The accompanying photographic drawing shows typical flower and foliage characteristics of 'Fip 440' with colors being as true as possible with an illustration of this type. The drawing depicts a side elevational view of a typical potted flowering plant of 'Fip 440'.

DETAILED BOTANICAL DESCRIPTION

The measurements were taken in Hillscheid, Germany, in mid May 2002, 10 weeks after planting of rooted cuttings. The plants were growing in 14 cm pots and had not been pinched.

In the following description color references are made to The Royal Horticultural Society Colour Chart. The color values were determined indoors from flowers developed in a green-house in May 2002 in Hillscheid, Germany.

INFLORESCENCE

Umbel:

*Shape.*—Semi-spherical.
*Average diameter.*—115 mm.
*Average depth.*—75 mm.
*Peduncle length.*—265 mm.
*Peduncle color.*—Light green, RHS 143 C, outdoors with a slight tinge of brown, RHS 179 A to 179 B.
*Pedicel length.*—33 mm.
*Pedicel color.*—Light green, RHS 143 C, near upper end weakly brownish infused, between RHS 179 B and 179 C.
*Number of flowers per umbel.*—About 30–40.

Corolla:

*Average diameter.*—42 mm.
*Form.*—Semi-double.
*Shape.*—Round outline, with the upper petals roughly the same size and shape as the lower petals, cup-shaped, open or with somewhat irregular directed inner petals.
*Number of petals.*—8–9.
*Number of petaloids.*—0–2, narrow, color RHS 40 A to 40 B.
*Shape of petals.*—Obovate, base acute, upper end is rounded, margin is entire.
*Size of petals.*—Upper petals: 24–26 mm long, 20–22 mm wide lower petals: 20–22 mm long, 23–24 mm wide.
*Color (general tonality from a distance of three meters)*.—Orange.
*Color of upper petals.*—Mainly RHS 40 A, near base lighter, RHS 41 B.
*Markings of upper petals.*—Very fine pink veins, RHS 47 B.
*Color of lower petals.*—RHS 40 B.
*Markings of lower petals.*—Absent.
*Color of lower surface of petals.*—Mainly orange, RHS 40 C, to light salmon-pink, RHS 43 D, marbled.
*Color of sepals.*—Both upper and lower surface: light green, RHS 144 B, near base brownish, RHS 179 B.
*Number of sepals.*—5.
*Shape of sepals.*—Linear to lanceolate, acute tip, truncate base, surface with very weak pubescence, margin entire.
*Size of sepals.*—10–12 mm long, 4 mm wide for the largest upper sepal, 2–3 mm in width for the other sepals.

Bud: (just prior to petals unfolding):

*Shape.*—Elliptical.
*Color of sepals.*—Light green, RHS 143 C.
*Color of petals.*—RHS 40 C.
*Length.*—17 mm.
*Width.*—10 mm.

Reproductive organs:

*Androecium.*—2–5 fertile anthers, moderate pollen, yellow-orange, RHS 26 A, filaments white, RHS 155 D.
*Gynoecium.*—One pistil, salmon-pink style and stigma, RHS 43 D, stigma 5–6-lobed.
*Fertility/seed set.*—No seed set observed.

Spring flower response period: In Hillscheid, Germany, in 2002 plants had on average 0.3 flowers opened 8 weeks after planting of rooted cuttings.

Outdoor flower production: Continuously flowering, the flower count in 2002 in Hillscheid, Germany, indicated about 3.2 inflorescence per plant in mid May.

Durability: Good stability of flower color, fair rain resistance.

Lastingness of the individual flower: About 8–9 days at 18° C., about 18 days for the umbel.

Fragrance: None.

PLANT

Foliage:

*Shape.*—Kidney-shaped with only very weak lobes, cordate base, with open gap between the lowest lobes.
*Margin.*—Bi-crenate.
*Texture.*—Upper surface smooth, dull, velvety.
*Size of leaf.*—120 mm wide, 68 mm long.
*Color of upper surface.*—Medium green, approximately RHS 137 B to RHS 137 C.
*Color of zonation.*—Brown, about RHS 166 A, distinctness: medium.
*Color of lower surface.*—RHS 137 D.
*Petioles.*—60–80 mm long, 3–3.5 mm diameter, light green in color, RHS 143 B to 143 C.

General appearance and form:

*Stem color.*—Green, RHS 143 B.
*Internode length.*—15–25 mm.
*Branching pattern.*—4.8 branches.
*Size of plants.*—Height 20.9 cm; width 31.7 cm (10-week-old plants, as described, measured from the top of the soil (base of the main stem) to the tips of the branches without inflorescences).

Pest/disease resistance/susceptibility: No observations to date.

I claim:

1. A new and distinct cultivar of geranium plant named 'Fip 440', as described and illustrated herein.

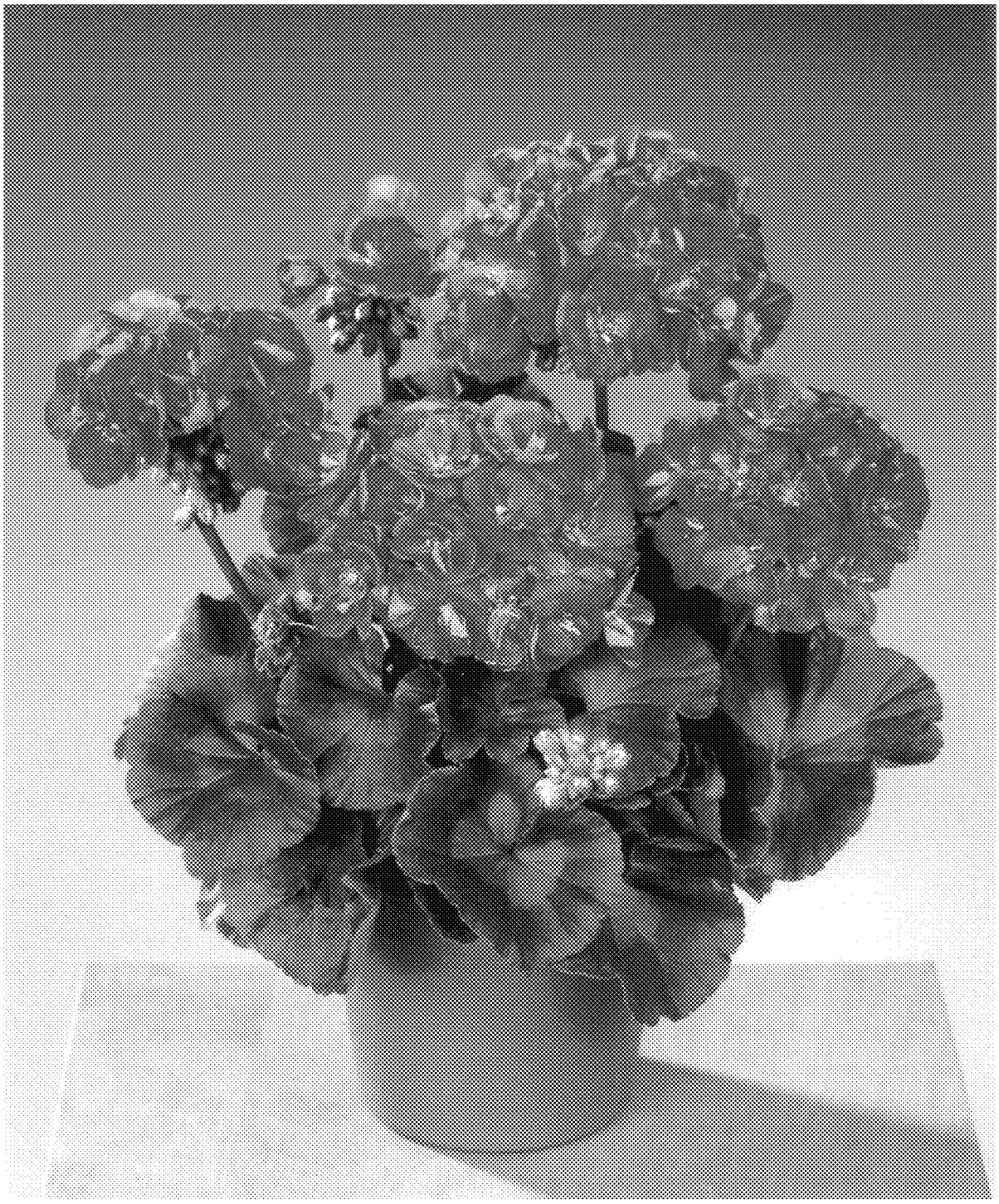

* * * * *